United States Patent [19]
Meitner

[11] Patent Number: 5,556,278
[45] Date of Patent: Sep. 17, 1996

[54] METHOD FOR MAKING AND USING A TEMPLATE FOR A DENTAL IMPLANT OSTEOTOMY AND COMPONENTS RELATING THERETO

[76] Inventor: Sean W. Meitner, 1077 Oakwood Dr., Victor, N.Y. 14564

[21] Appl. No.: 302,344

[22] Filed: Sep. 7, 1994

[51] Int. Cl.⁶ ............................................. A61C 3/00
[52] U.S. Cl. ................................. 433/75; 433/213
[58] Field of Search ........................ 433/72, 74, 75, 433/76, 213

[56] References Cited

U.S. PATENT DOCUMENTS

| | | |
|---|---|---|
| 2,434,320 | 1/1948 | Karlstrom . |
| 3,011,259 | 12/1961 | Baum . |
| 3,407,503 | 10/1968 | Nealon . |
| 3,413,724 | 12/1968 | Segal . |
| 3,600,810 | 8/1971 | Castlecrag et al. . |
| 4,060,899 | 12/1977 | Sauter .................................... 433/74 |
| 5,007,836 | 4/1991 | Gayso .................................... 433/181 |
| 5,015,183 | 5/1991 | Fenick .................................... 433/76 |
| 5,133,660 | 7/1992 | Fenick .................................... 433/76 |

FOREIGN PATENT DOCUMENTS

4026200  11/1994  WIPO ..................................... 433/75

Primary Examiner—Cary E. O'Connor
Attorney, Agent, or Firm—Cumpston & Shaw

[57] ABSTRACT

A method for making a template for use in a dental implant recipient's mouth whereby the template includes a guide sleeve for orienting a drill bit in a desired location and angulation for making an implant osteotomy in the recipient's maxilla or mandible. The method includes the steps of making a cast impression of the recipient's arch, drilling a hole in the cast arch substantially corresponding to the prospective osteotomy, inserting a guide post in the hole, locating a guide sleeve over the guide post; applying a resinous, template forming material on the cast arch around the guide sleeve; allowing the template material to cure to form the template; removing the guide post from the cast arch; removing the cured template from the cast arch and placing it in the patient's mouth; and radiographically visualizing the guide sleeve in the patient's mouth.

44 Claims, 4 Drawing Sheets

METHOD FOR MAKING AND USING A TEMPLATE FOR A DENTAL IMPLANT OSTEOTOMY AND COMPONENTS RELATING THERETO

BACKGROUND OF THE INVENTION

1. Field of the Invention

The invention relates to a method for precisely locating a dental implant hole (osteotomy) in a patient's jawbone by construction and use of a template, and to the template and guide sleeve components thereof.

2. Description of Related Art

One aspect of contemporary dental surgery involves the use of prosthetic teeth to replace missing teeth. Typically one or more prosthetic teeth are mounted on dental implants which are secured in the jawbone of the recipient. The dental implants must be securely mounted in sufficient bone tissue so that they are as stable as natural teeth roots.

The conventional procedure for installing a dental implant includes drilling a hole in the maxillary or mandibular jawbone of the recipient, inserting the implant in the hole, and attaching a prosthetic tooth to the implant. Various types of dental implants are used; for example, blades, screws, and cylinders. The dental implant is generally made of titanium or high titanium alloy and the top of the dental implant, which is typically located at the gingiva, is provided with a mating means (usually a top portion and inner threads) for attaching the prosthetic tooth thereto.

The osteotomy must be located the correct distance from adjacent teeth in order to guarantee a proper fit and cosmetic result for the prosthetic device. Furthermore, it is extremely important to accurately locate the osteotomy in the jawbone so that the implant is sufficiently anchored in the bone structure of the patient's jaw.

Because of the limited space, working within a patient's mouth poses many impediments to easily and precisely locating and making the osteotomy for the implant, and ultimately positioning the prosthetic.

It is known in dental surgery to make a cast impression of the patient's mandible and/or maxilla in order to design or select the appropriate prosthetic device. Moreover, it is known to use a diagnostic tooth set-up or wax-up on a cast to determine the most desirable tooth position in the final restoration. In locating and creating the hole for a dental implant, however, the most commonly used method is simply to survey the area visually and drill according to visual inspection. In some cases, where the patient is completely or significantly toothless, an acrylic tooth set-up may be used in the patient's mouth to locate the most desirable tooth position in the final restoration. With acrylic tooth set-ups, the surgeon drills through the tooth set-up in order to make a mark On the patient's jawbone. The acrylic set-up is then removed, and the mark is used as the start of the hole for the implant. In other words, the surgeon continues drilling the started hole at a visually determined angle.

Other techniques for locating dental implants are available. Fenick, for example, in U.S. Pat. No. 5,051,183, describes a method involving the use of a casting having a radiopaque marker which is inserted into the patient's mouth. A series of X-rays is then taken to establish a trajectory for the proposed osteotomy in the patient's jawbone. While the method provides an accurate means to locate the implant hole, it requires multiple x-rays subjecting the patient to undesirable exposure levels, and is expensive.

Accordingly, the inventor has recognized a need for a method and apparatus for accurately, safely, and conveniently locating an osteotomy for a dental implant in the mouth of the implant recipient.

SUMMARY OF THE INVENTION

It is therefore an object of the invention to provide a method for accurately locating one or more dental implant osteotomies in an implant recipient's jawbone;

it is another object of the invention to provide a method for determining the angulation and positioning of dental implants to optimize the functional and aesthetic aspects of a prosthetic tooth or teeth;

it is a further object of the invention, in conjunction with the method for locating the osteotomy, to provide a template that acts as a guide for the surgeon to direct and maintain the planned orientation of a drill bit in relation to the anatomical structures of the recipient during the creation of an osteotomy site; and it is a still further object of the invention to provide a method for locating an implant osteotomy in a jawbone that allows the use of an inexpensive, household quality drill bit in a straight dental handpiece for making a pre-osteotomy implant guide hole in a cast arch.

In accordance with the forgoing objects, the present invention includes a method for locating a dental implant osteotomy in an edentulous space of a patient's mandible or maxilla (arch), involving the steps of making a cast impression of the patient's mandible and maxilla including the edentulous space; temporarily locating an appropriate number of diagnostic tooth set-ups in the edentulous space or spaces of the cast arch, each corresponding to an optimum location of a prosthetic tooth in the edentulous space; drilling a hole through the tooth set up and into the cast arch wherein the hole in the arch corresponds to an optimum location and orientation of the proposed osteotomy in the patient's jaw bone; removing the drilled through tooth set up from the cast arch after the hole has been drilled; inserting a guide post into the hole; locating a guide sleeve over a part of the guide post projecting up from the hole; applying a template forming, molding material over a selective portion of the cast arch including the area around the sleeve or sleeves for forming a template having one or more drill bit guide sleeves embedded therein; allowing the template forming material to cure; removing all, or all but at most one, guide posts from the corresponding holes in the cast arch; removing the cured template including the guide sleeve or sleeves embedded therein from the cast impression; and seating the template in the patient's jaw where it can be evaluated radiographically for accurately providing a drill guide for the surgeon to make the osteotomy.

A person skilled in the art will be able to determine the extent of the arch necessary to be cast; i.e., whether the cast impression need include one or more teeth adjacent the edentulous space, or the entire maxilla or mandible of the recipient; and the size or extent of the template for ultimate use in the patient's mouth.

The invention also includes the step of radiographically visualizing the correct location and orientation of the radiopaque guide sleeve in the patient's mouth in an oblique, horizontal or axial plane via a panorex radiograph, computer assisted tomography (CAT scan), linear tomography, periapical x-ray, or other internal visualization technique, and using the resulting visualization in conjunction with the cast arch impression to evaluate and if necessary, change, the position of the guide sleeve in a horizontal and/or an oblique plane prior to preparing the osteotomy site.

The invention further includes the step of applying a non bonding, separating medium such as wax, or other suitable material, on the cast arch in the edentulous space and on the cast tooth surfaces wherever the template forming material will be applied to facilitate removal of the template from the cast impression once the template is cured.

The method thus described is not limited to the location of a single implant osteotomy, but the technique applies equally to locating more than one implant osteotomy in one or more edentulous spaces in a patient's mouth.

The template used for locating the osteotomy according to the invention comprises a cured, resinous base, the underside contour of which corresponds to the implant recipient's jaw bone including the edentulous space. The material of the template is a self-curing or light-curing resin or other material suitable for the construction of dental templates. The template also includes at least one guide sleeve partially embedded in the base in an orientation such that when the template is inserted into the patient's mouth, the sleeve provides a precise guide for the drill bit used by the surgeon in drilling the osteotomy in the patient's jaw bone.

In one aspect of the invention, the guide sleeve comprises a right circular cylindrical sleeve; i.e., a sleeve having a straight cut terminal end and a straight cut base end. The sleeve has a bore sufficient in diameter to allow the sleeve to be slid over a guide post (described below) and to ultimately accommodate a drill it therethrough with a minimum of lateral movement of the drill bit. In an aspect of this embodiment, the sleeve has one or more slots cut into a front portion of the sleeve for irrigation or to aid the surgeon in visualizing the drilling of the osteotomy. The slot(s) are oriented longitudinally and are spaced apart from the ends of the sleeve. A set of wing members project transversely from a rear portion of the sleeve to provide additional surface area for securing the sleeve in the template forming resin.

In another embodiment, the guide sleeve has a straight cut base end and a diagonally cut terminal end. When the implant is to be located in a posterior region of the patient's mouth where the inter arch space is reduced, the diagonally cut guide sleeve provides more room in the patient's mouth for the drilling apparatus and for maneuvering the drill bit into the guide sleeve bore. In one aspect of the diagonally cut guide sleeve embodiment, the sleeve includes one or more parallel sets of wing members similar to the wing members described for the slotted, straight cut sleeve.

All of the sleeve embodiments are preferably constructed of stainless steel, titanium, or non x-ray scattering ceramic.

The invention also contemplates the use of guide posts. A first section of a guide post is inserted into the hole in the cast arch after drilling. A second section of the guide post extends above the simulated gum line of the cast arch providing a structure over which a guide sleeve can be located. Once the template forming material has been applied to the cast arch and around the guide sleeve, and before the template is removed from the arch, the one or more guide posts, each of which occupy a hole in the cast arch, is removed from the arch. The guide post therefore acts as a guide for the angular orientation and positioning of the guide sleeve in the template, and ultimately for the drill bit during drilling of the osteotomy. In one aspect of the invention, a guide post comprises a first section having a length and diameter sufficient for occupying the hole in the cast arch with a minimum of lateral movement. A second section of the post having a larger diameter than that of the first section extends from the end of the first section and projects above the simulated gum line of the patient's jaw bone when the post occupies the hole. The diameter of the second section is sufficient to allow the guide sleeve to be slid over the second section of the guide post without significant residual lateral movement, thus allowing the post to be removed from the hole after the guide sleeve is secured in the template forming material but prior to removing the cured template from the cast arch.

In another aspect of the guide post, the post includes a third section projecting from the end of the second section, and having a diameter smaller than the diameter of the second Section. It will be appreciated by one skilled in the art that if one or more guide posts are inserted into the cast arch at a significant angle, it will not be possible to remove the template from the cast arch until the guide post is first removed from the hole. Since the second section of the guide post is typically the same length as the guide sleeve, the third section of the guide post provides a grasping surface for removing the post from the hole prior to removing the cured template from the cast arch.

The invention will now be described in detail in terms of the drawings and the description which follow.

DETAILED DESCRIPTION OF THE INVENTION

Figure 1:
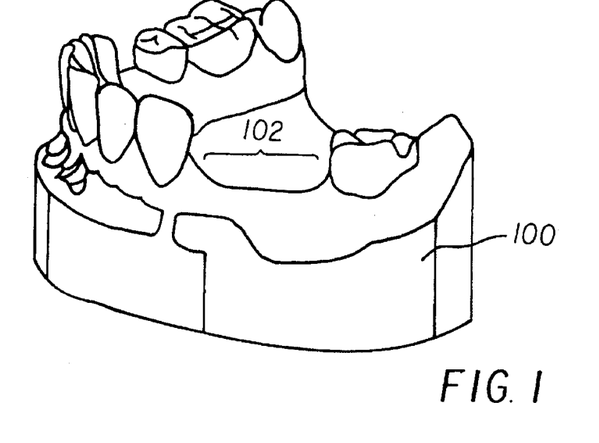
FIG. 1 is a perspective view of a cast impression of a portion of a human mandibular jawbone (arch) showing a number of teeth and an edentulous space where one or more prosthetic teeth will be located.

Referring now to FIG. 1, a method for locating a dental implant osteotomy in an edentulous space of a patient's mandible or maxilla comprises first creating a cast impression 100 of the patient's mandible or maxilla jaw bone (arch) having an edentulous space 102 where at least one tooth is missing and is to be replaced by a prosthetic tooth via a dental implant. The impression of the partially edentulous arch and, optionally, the opposing arch, is typically made in alginate and poured up, preferably, in cast stone. Cast stone is preferred over die stone because the relatively softer cast stone permits the use of a household quality drill bit for making the implant guide hole in the cast arch, as will be more fully described below.

Figure 2:
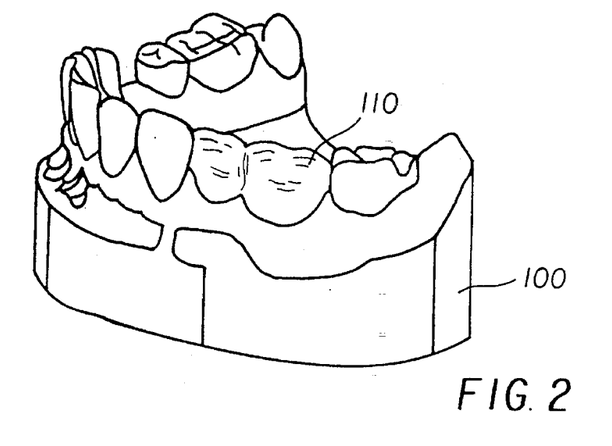
FIG. 2 is a view similar to FIG. 1 but showing two diagnostic tooth set-ups located in the edentulous space of the cast arch.

A diagnostic tooth set up 110 made from wax or other material well known to those skilled in the art is temporarily located in the edentulous space 102 of the cast arch 100, as shown in FIG. 2. The edentulous space 102 depicted in FIG. 1 has received two adjoining diagnostic tooth set ups 110 in FIG. 2, and it is to be understood throughout this specification that the invention is not limited to merely a single implant, but comprises methods and apparatus for either a single or multiple implants, thus the figures illustrate the method of the invention for two adjacent implants.

Typically, a cast impression of the opposing arch (not shown) is also prepared and both cast arctics will be mounted on an articulator so that the optimum size, location and position of the prosthetic tooth or teeth can best be determined.

Since a rigid template will be formed by applying a resinous molding material over a portion of the partially edentulous arch, as will be more fully described below, at any point in the process described herein a layer of non bonding, separating material 116 such as wax or other suitable medium well known to those skilled in the art is applied to the surface of the cast arch 100 wherever the template forming material 136 will be applied, so that upon curing of the template forming material the template 140 can easily be removed from the cast arch 100.

Figure 3:
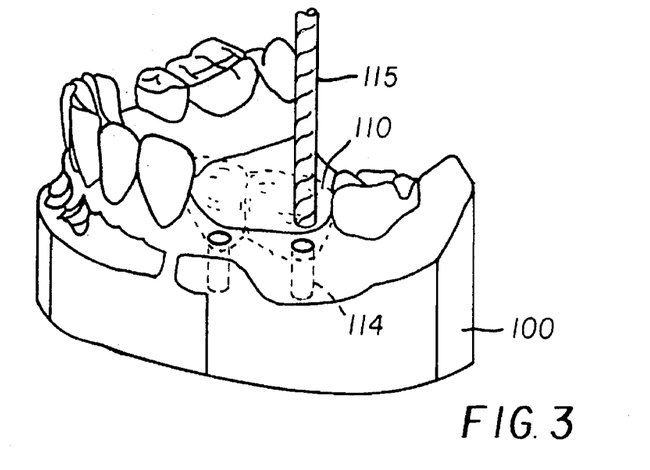
FIG. 3 is a view similar to FIG. 2 but showing a household type drill bit extending through one (for clarity) of the tooth set-ups, and the resultant guide post holes in the cast arch.

As shown in FIG. 3, a hole 114 is drilled with a drill bit 115 through each of the diagnostic tooth set ups 110 and into the base of the cast arch 100. The hole 114 corresponds to the prospective osteotomy in the patient's real arch and therefore the location and orientation of the hole will correspond to an optimum location and orientation of the implant osteotomy. The hole in the cast arch is preferably made with a standard, inexpensive ³⁄₃₂'s inch diameter drill bit which conveniently fits in a dental laboratory handpiece.

The depth of the hole is preferably at least 10 mm., and the hole 114 in the cast arch has a smaller diameter than that of the osteotomy.

Figure 4:
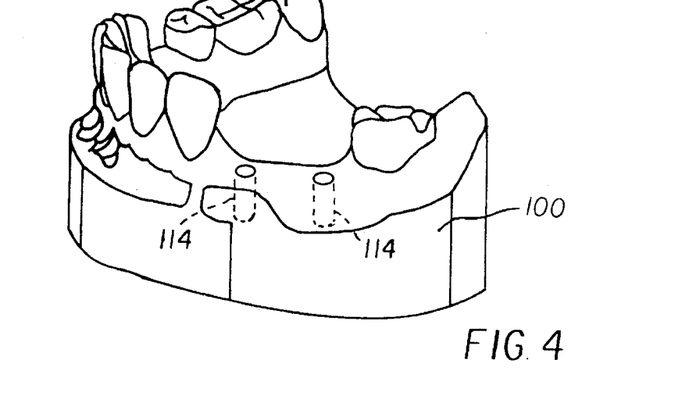
FIG. 4 is a view similar to FIG. 1 but showing the drilled holes in the cast arch.
Figure 5:
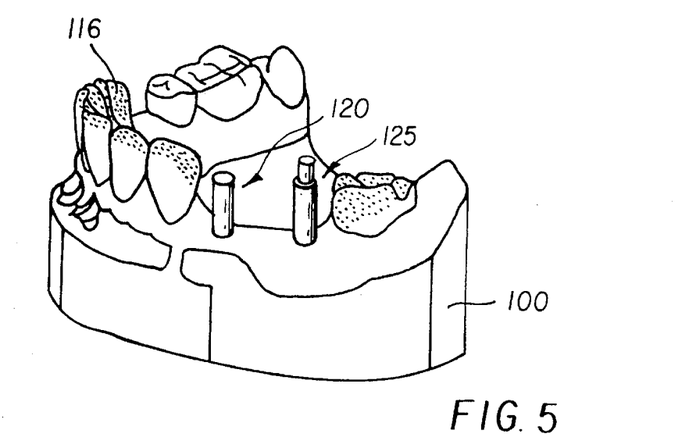
FIG. 5 is a perspective view of the cast arch showing a shorter, two-section guide post and a longer, three-section guide post, each inserted into one of the holes in the cast arch of FIG. 4, and a layer of non-bonding medium applied to selected portions of the cast arch, the teeth and the edentulous space.

Once the hole 114 is drilled in the cast arch 100, the diagnostic tooth set up 110 is removed from the edentulous space leaving the hole 114 in the area of the alveolar ridge in the position desired for the center of the implant, as shown in FIG. 4. A layer of non bonding, separating material 116 is preferably now applied to the cast arch including the edentulous space, and a guide post is inserted into each hole as shown in FIG. 5. Different guide post designs, illustrated in FIGS. 10 and 11, each of which is appropriate for a particular type and location of implant, will now be described.

Figure 10:
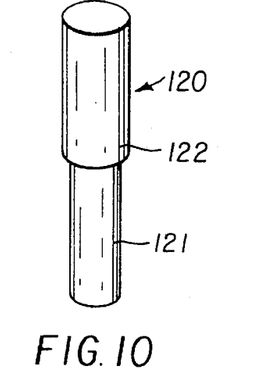
FIG. 10 is a perspective view of a two section guide post having a smaller diameter, hole occupying part and a larger diameter, projecting part.

In FIG. 10, a post 120 is shown having a smaller diameter first section 121 and a larger diameter second section 122. The outer diameter of the first section 121 is sufficient to allow the first portion to slidably engage the hole 114 in the cast arch such that there is a minimum amount of lateral movement between the post and the hole, but so that the post can be easily removed from the hole when desired. When the hole in the arch has been drilled with a ³⁄₃₂'s inch drill, the first portion 121 of the guide post 120 will preferably have a diameter of 0.091 inch (2.33 mm) and the second portion 122 of the guide post 120 will have a diameter preferably of 0.125 inch (3.18 mm). It will be appreciated by one skilled in the art that the criticality of the post diameters will depend on the size of the implant hole and the size of other hardware to be described below, and will in general be dictated by the sizes of drill bits conventionally used for drilling implant osteotomies. In a preferred aspect of the post embodiment thus described, the length of the first section 121 is 10 mm and the length of the second section 122 is 6 mm, such that the total guide post length is 16 mm. In another preferred aspect, both sections 121, 122 of the guide post are 10 mm in length, making the total guide post length equal to 20 mm. The appropriate length guide post can be determined by inserting the post in the hole in the cast arch and mounting the opposing arches on an articulator. The guide pins should be short enough so that the casts can be articulated fully to see the relationship of the center of the guide post to the cusps of the teeth in the opposing arch (not shown).

Figure 11:
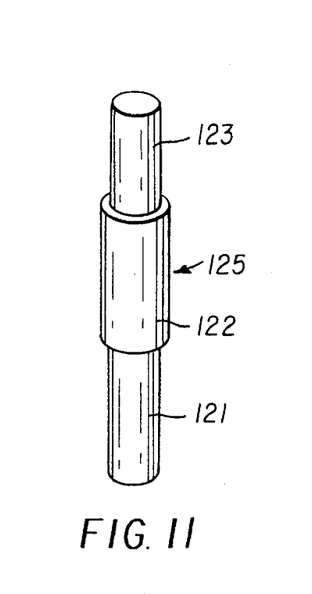
FIG. 11 is a perspective view of another embodiment of the guide post having a first, smaller diameter, hole occupying section, a second, larger diameter section, and a third section having a diameter less than that of the second section.

A second guide post embodiment is shown in FIG. 11. The guide post 125 of FIG. 11 is identical to that illustrated in FIG. 10 except that a third section 123 having a diameter less than the diameter of the second section 122 extends from a top Surface of the second section 122. In a preferred aspect of this embodiment, the diameter of the third section is the same as the diameter of the first section, and the third section is 10 mm in length, giving the guide post 125 a total length of either 26 mm or 30 mm.

In use, the first section 121 of either of the guide posts shown in FIGS. 10 and 11 is inserted into the hole 114 in the cast arch while the remaining section(s) of the guide post project up from the base of the edentulous space of the arch as Shown in FIG. 5. A two section guide post 120 will preferably be used when a template for a single implant is made. The three section post 125 is used when a template will be made for two or more implants, as the third section 123 of the guide post 125 provides a grasping surface that allows the post to be removed from the cast arch prior to removing the cured template 140 from the arch, as will be more fully described below. FIG. 5 thus shows the cast arch having a two section guide post 120 and a three section guide post 125 located in adjacent edentulous spaces of the cast arch.

Figure 6:
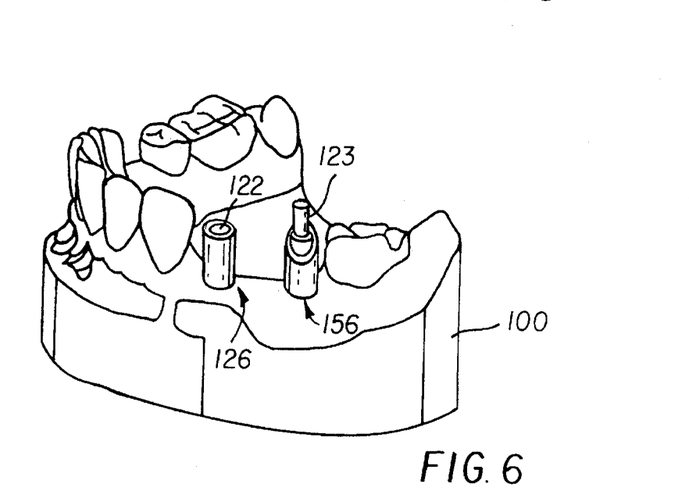
FIG. 6 is a view similar to FIG. 5 but showing a guide sleeve having a diagonally cut terminal end installed over the longer guide post, and a cylindrical guide sleeve installed over the shorter guide post and flush with the top of the post.
Figure 12:
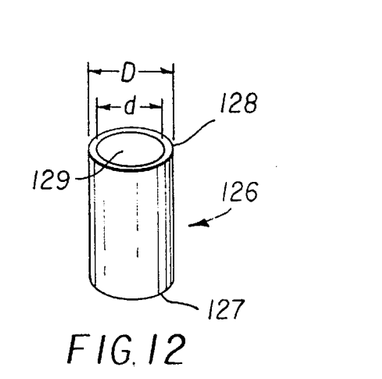
FIG. 12 is a perspective view of a cylindrical guide sleeve having plane cut base and terminal ends.
Figure 13:
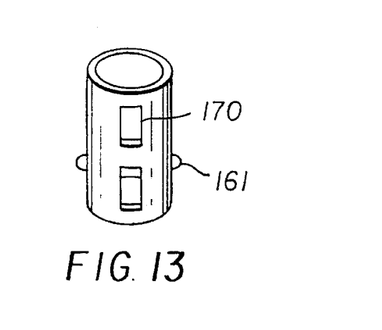
FIG. 13 shows a slotted guide sleeve including a set of wing members on the back of the sleeve.
Figure 16:
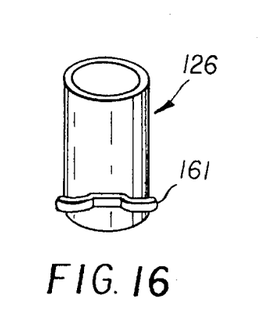
FIG. 16 is a rear elevational view of the slotted guide sleeve of FIG. 13 showing the set of wing members.

Referring now to FIG. 6, a guide sleeve is slid over the projecting part of the guide post until a base end of the sleeve rests in contact with the cast arch. Several different sleeve embodiments are shown in FIGS. 12–15 and each of them will now be described. In one embodiment, as shown in FIG. 12, a guide sleeve 126 comprises a right circular cylindrical sleeve; i.e., a sleeve having a straight cut base end 127 and a straight cut terminal end 128. In a preferred aspect of this embodiment, the sleeve has one or more longitudinally oriented slots 170 in a front portion of the sleeve wall, as shown in FIG. 13. The slot or slots are displaced from the ends of the sleeve and provide an opening for irrigating the osteotomy during drilling if the dental handpiece is not self irrigating; and allow the surgeon to better visualize the drilling procedure. The slotted sleeve further includes a set of wing members 161, as shown in FIGS. 13 and 16, that project transversely from a rear portion of the sleeve surface, and provide additional surface area for securing the sleeve in the template forming resin since the slots preclude encircling the slotted sleeve with the resin.

Figure 14:
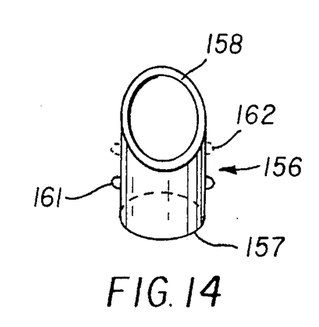
FIG. 14 is a from elevational view of a cylindrical guide sleeve having a plane cut base end and a diagonally cut terminal end, including a set of wing members and an optional set of wing members shown in phantom.
Figure 15:
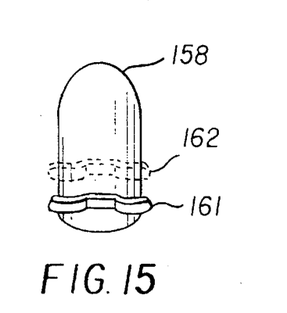
FIG. 15 is a rear elevational view of the diagonally cut guide sleeve of FIG. 14.

In a second embodiment, as shown in FIG. 14, a cylindrical guide sleeve 156 has a straight cut base end 157 and a diagonally cut terminal end 158. A set of wing members 161 project transversely from a rear portion of the sleeve surface to provide additional surface area for securing the sleeve in the template forming material as will be described more fully below. In an aspect of this embodiment, the sleeve may have a second set of wing members 162, shown in phantom in FIG. 14, projecting from the sleeve parallel to the first set to provide additional surface area for the diagonally cut guide sleeve.

In each of the embodiments of the guide sleeves 126, 156 shown, the diameter, d, of the bore of the sleeve will be sufficient to allow the sleeve to be slid over the projecting section 129 of the guidepost having the largest diameter, as illustrated in FIG. 6. For the drill bit and guide post dimensions mentioned above, the diameter of the bore 129 in the sleeve will preferably be 3.20 mm, and the outer diameter, D, of the sleeve will preferably be 3.75 mm. The overall length of the straight cut guide sleeve is preferably 10 mm; while for the diagonally cut guide sleeve, the length from the base of the sleeve to the low end of the diagonal cut will be 8 mm and from the base of the sleeve to the top of the diagonal cut will be 10 mm.

It will be appreciated by a person skilled in the art that the straight cut guide sleeve 126 is more suitable for use in anterior regions of the patient's mouth where the inter arch space is greatest, and that the diagonally cut guide sleeve 156 will be more suitably used in the posterior regions of the arch where the decreased amount of inter arch space restricts the available space for maneuvering the drill.

The guide sleeve embodiments described herein are preferably constructed of a durable, sterilizable material such as stainless steel or titanium. In one aspect of the straight cut guide sleeve embodiment used with a CAT scan radiograph, the sleeve is preferably constructed of a ceramic material which does not scatter x-rays and blur the resulting radiograph the way a metal sleeve would.

Figure 7:
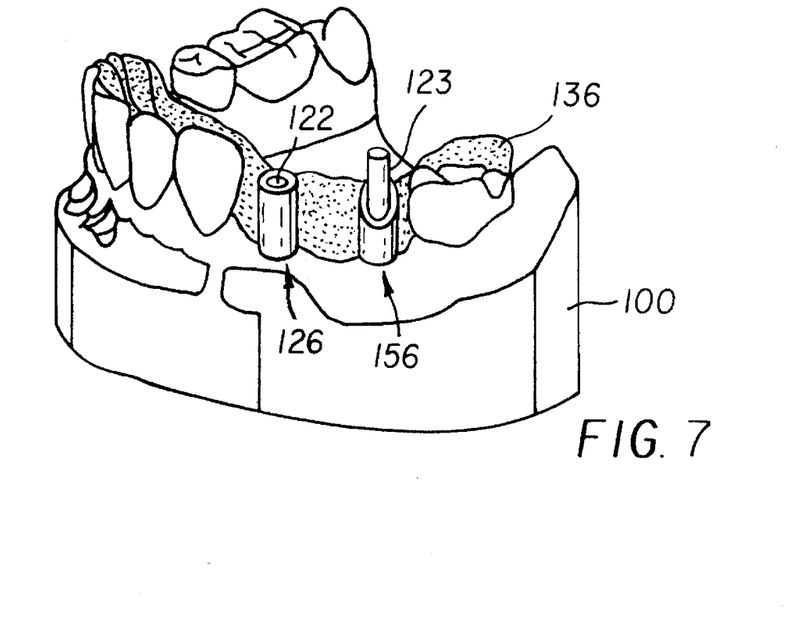
FIG. 7 shows a resin template molding material applied to the cast arch in and around the guide sleeves, the edentulous space and adjoining teeth, for forming the template.

Referring now to FIG. 7, a moldable, template forming material 136 is applied to the cast arch 100 around the sleeves in the edentulous space and around at least one tooth adjacent each side of the edentulous space. The extent of the template material around adjacent teeth will be determined by the amount of stability required of the template and can be suitably determined by one having ordinary skill in the art when the template is being constructed. The template material 136 will preferably be a self curing, or light curing, resin although any suitable material can be used. It will now be appreciated that the one or more wings 161 projecting from the wall of the diagonally cut sleeve 156 will help anchor the sleeve in the resinous material since the overall surface area for bonding the diagonally cut sleeve with the template material is less than that for the straight cut sleeves.

Figure 8:
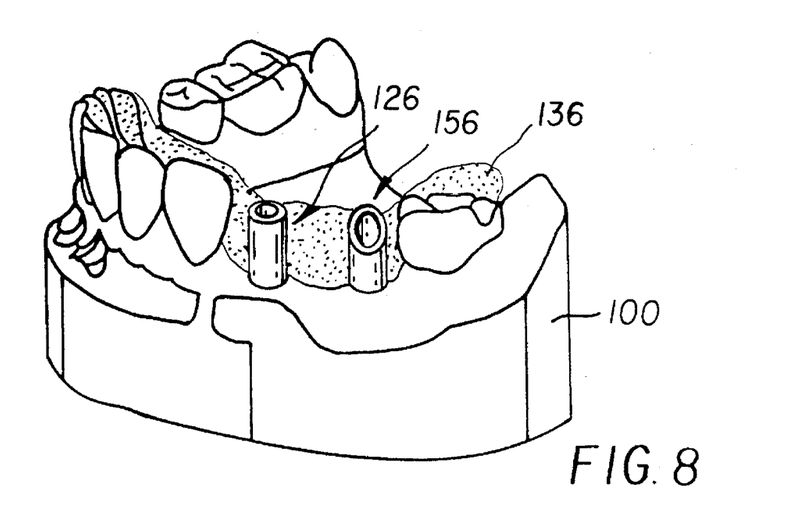
FIG. 8 is a view similar to FIG. 7 with the longer guide post removed from the hole, and the guide sleeves embedded in the resin template molding material.

After, or during, the curing of the resin 136, all, or at least all but one of the guide posts are removed from the cast arch leaving the template and the guide sleeve embedded therein resting on the arch, as shown in FIG. 8. Since the length of the projecting part of the two section guide post is not greater than the length of the straight cut sleeve, it will not be possible to remove the guide post encircled by the straight cut sleeve from the cast before the template is removed; moreover, if the template has two or more guide sleeves embedded therein and there are corresponding guide posts in the holes in the cast arch, it may not be possible to remove the template and the guide sleeves until all but at least one of the guide posts are first removed. This is particularly the case when the guide posts are positioned in the cast arch at an angle. The reader will thus appreciate that the third section 123 of the guide post 125 provides a convenient grasping surface which allows the guide post to be removed from the cast arch prior to removing the template.

Figure 9:
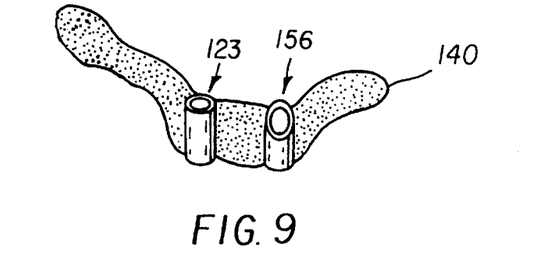
FIG. 9 is a perspective view of the template including the guide sleeves embedded therein after removal of the cured template from the cast arch, and ready to be put into the recipient's mouth.

Once the resin has cured; the template 140 including the guide sleeve or sleeves embedded therein, is removed from the cast arch and appears as schematically shown in FIG. 9, ready for use in the patient's mouth. As shown in FIG. 9, the template 140 includes a straight cut guide sleeve 126 and a diagonally cut guide sleeve 156 corresponding to edentulous spaces in the cast; however, as described above, the template 140 can be created for either one or multiple implants.

The template 140 can now be inserted into the patient's mouth and the position and orientation of the guide sleeve or sleeves can be radiographically visualized before the osteotomy is drilled. This can be accomplished by taking one of a panorex, linear tomograph, or periapical x-ray or CAT scan. The information obtained from such an evaluation can be used to confirm or alter the parameters of the guide sleeve to provide the optimum drilling position for the osteotomy.

There has thus been described a method for locating a dental implant osteotomy in a patient's jawbone; a method for forming a template used for optimizing the location and position of the osteotomy; and apparatus used in conjunction with the above described methods. Those skilled in the art will recognize that modifications may be made in the method and apparatus described herein without departing from the true spirit and scope of the invention which accordingly are intended to be limited solely by the appended claims.

I claim:

1. A method for locating a dental implant osteotomy in an edentulous space of a patient's mandible or maxilla, comprising the steps of:

forming a cast arch including the edentulous space;

temporarily locating a diagnostic tooth set-up in the edentulous space of the cast arch corresponding to a desired location of a prosthetic tooth in the edentulous space of the patient's mandible or maxilla; and drilling a hole through the tooth set-up and into the cast arch wherein the location and orientation of the hole correspond to an optimum location and orientation of the dental implant osteotomy.

2. The method according to claim 1 in which the step of forming a cast arch including the edentulous space includes casting an impression of a tooth adjacent one side of the edentulous space where the dental implant will be located.

3. The method according to claim 1 in which the step of forming a cast arch including the edentulous space includes casting an impression of at least one tooth adjacent one sides of the edentulous space where the implant will be located, and of at least one tooth adjacent another side of the edentulous space.

4. The method of claim 1, further comprising the steps of:

removing the drilled-through tooth set-up from the cast arch;

inserting a guide post into the hole;

locating a guide sleeve over a projecting part of the guide post;

applying a template forming, molding material over a selected region of the cast arch and around the guide sleeve;

allowing the molding material to cure;

removing the guide post from the cast arch; and removing the cured template including the guide sleeve embedded therein from the cast arch, whereby using the template in the patient's mouth provides a guide means for drilling the osteotomy.

5. The method of claim 4 further comprising applying a layer of a non-bonding, separating medium over a selected region of the cast arch including the edentulous space and adjacent regions where a template forming material will be applied prior to applying the template forming, molding material to the arch.

6. The method according to claim 4 in which the step of forming a cast arch including the edentulous space includes casting an impression of a tooth adjacent one side of the edentulous space where the dental implant will be located.

7. The method according to claim 4 in which the step of forming a cast arch including the edentulous space includes casting an impression of at least one tooth adjacent one side of the edentulous space where the implant will be located, and of at least one tooth adjacent another side of the edentulous space.

8. The method according to claim 4, further comprising the step of radiographically visualizing the location and orientation of the guide sleeve seated in the template positioned in the patient's mouth.

9. The method according to claim 8 in which the step of radiographically visualizing the location and orientation of the guide sleeve comprises making one of a Panorex radiograph, a periapical x-ray, a linear tomograph and a CAT scan.

10. A method according to claim 4 wherein the molding material comprises a curable resin.

11. A method according to claim 10 wherein the curable resin comprises one of a self-curing resin and a light-curing resin.

12. A method for making a template for use in a patient's mouth for locating more than one dental implant osteotomy in two or more edentulous spaces of the patient's mandible or maxilla, comprising the steps of:

forming a cast arch including more than one edentulous space;

temporarily locating a diagnostic tooth set-up in each edentulous space of the cast arch corresponding to a desired location of a prosthetic tooth in each edentulous space of the patient's mandible or maxilla;

drilling a hole through each of the tooth set-ups and into the cast arch wherein the location and orientation of each of the holes correspond to a desired location and orientation of each of the dental implant osteotomies;

removing the drilled-through tooth set-ups from the cast arch;

inserting a guide post into each hole;

locating a guide sleeve over a projecting part of each of the guide posts;

applying a template forming, molding material to selected regions of the cast arch and around the guide sleeves;

allowing the molding material to cure;

removing all but at most one of the guide posts from the cast arch; and removing the cured template including the guide sleeves embedded therein from the cast arch, whereby using the template in the patient's mouth the guide sleeves provide guide means for drilling the osteotomies.

13. The method according to claim 12 further comprising applying a layer of a non-bonding, separating medium over a selected region of the cast including the edentulous spaces and adjacent regions where a template forming material will be applied.

14. The method according to claim 12 in which the step of obtaining a cast arch including the more than one edentulous space includes casting an impression of a tooth adjacent one side of each of the edentulous spaces where the dental implant will be located.

15. The method according to claim 12 in which the step of obtaining a cast arch including the more than one edentulous space includes casting an impression of at least one tooth adjacent one side of each of the edentulous spaces where the implant will be located, and of at least one tooth adjacent another side of the edentulous spaces.

16. The method according to claim 12, further comprising the step of radiographically visualizing the location and orientation of the guide sleeves seated in the template positioned in the patient's mouth.

17. The method according to claim 16 in which the step of radiographically visualizing the Location and orientation of the guide sleeves comprises making one of a Panorex radiograph, a periapical x-ray, a linear tomograph and a CAT scan.

18. A method according to claim 12 wherein the molding material comprises a curable resin.

19. The method according to claim 18 wherein the curable resin comprises one of a self-curing and a light-curing resin.

20. A template for locating a dental implant osteotomy in a patient's mandible or maxilla having an edentulous space, comprising: a cured, resinous base having an impression of the patient's mandible or maxilla including the edentulous space;

a guide sleeve at least partially embedded in the base and projecting through a top surface thereof, having a bore sufficient to receive a drill bit for making the osteotomy, in which the sleeve is fixed in the base in a position and at an angle corresponding to the optimum position and angle of the osteotomy; and a set of wing members projecting transversely from a rear surface of the guide sleeve.

21. The template of claim 20 in which the guide sleeve is a cylinder having a straight cut base end and a terminal end.

22. The template of claim 21 in which the terminal end is straight cut.

23. The template of claim 21 in which the terminal end is diagonally cut.

24. The template of claim 23 a second set of wing members disposed on the rear surface of the sleeve parallel to the set of wing members.

25. The template of claim 20 in which the guide sleeve is constructed from one of stainless steel and titanium.

26. The template of claim 20 in which the guide sleeve is ceramic.

27. The template of claim 20 in Which the guide sleeve has a slot in a front surface of the guide sleeve and spaced apart from the end of the sleeve.

28. The template of claim 27 which the slot is longitudinally oriented in the sleeve.

29. Apparatus used in forming a template for locating a dental implant osteotomy in a patient's mandible or maxilla, comprising:

a cylindrical guide post including a first section having a first diameter and a first length, and a second section having a second length extending from an end of the first section and having an enlarged portion with a second diameter greater than the first diameter; and a guide sleeve having a cylindrical bore with diameter greater than the second diameter and a length less than or equal to the second length.

30. The apparatus of claim 29 in which the second section further comprises a reduced portion having a diameter less than the diameter of the enlarged portion, extending from and end of the enlarged portion of the second section remote from the first section.

31. The apparatus of claim 29 in which the guide sleeve is a cylinder having a straight cut base end and a terminal end.

32. The apparatus of claim 31 in which the terminal end is straight cut.

33. The apparatus of claim 31 in which the terminal end is diagonally cut.

34. The apparatus of claim 29 in which the guide sleeve is ceramic.

35. The apparatus of claim 29 in which the guide sleeve is one of stainless steel and titanium.

36. The apparatus of claim 29 in which the guide sleeve includes a set of wing members projecting transversely from a rear surface of the sleeve.

37. The apparatus of claim 29 in which the guide sleeve has a slot in a front surface of the guide sleeve and spaced apart from the end of the sleeve.

38. The apparatus of claim 37 in which the slot is longitudinally oriented in the sleeve.

39. A template for locating a dental implant osteotomy in a patient's mandible or maxilla having an edentulous space, comprising:

a cured, resinous base having an impression of the patient's mandible or maxilla including the edentulous space;

a guide sleeve at least partially embedded in the base in a position and at an angle corresponding to the optimum position arid angle of the osteotomy and projecting through a top surface thereof, having a bore sufficient to receive a drill bit for making the osteotomy, in which the sleeve is fixed in the base; and a slot in a front surface of the guide sleeve and spaced apart from the end of the sleeve.

40. The template of claim 39 in which the guide sleeve is a cylinder having a straight cut base end and a terminal end.

41. The template of claim 40 in which the terminal end is straight cut.

42. The template of claim 41 in Which the terminal end is diagonally cut.

43. Apparatus used in forming a template for locating a dental implant osteotomy in a patient's mandible or maxilla, comprising:

a cylindrical guide post including a first section having a first diameter and a second section extending from an end of the first section having a second diameter greater than the first diameter; and a guide sleeve having a cylindrical bore with a diameter greater than the second diameter; and a set of wing members disposed intermediate the ends of the guide sleeve and projecting transversely from a rear surface of the guide sleeve.

44. Apparatus used in forming a template for locating a dental implant osteotomy in a patient's mandible or maxilla, comprising:

a cylindrical guide post including a first section having a first diameter and a second section extending from an end of the first section having a second diameter greater than the first diameter; and a guide sleeve having a cylindrical bore with a diameter greater than the second diameter; and a slot in a front surface of the guide sleeve and spaced apart from the end of the sleeve.

* * * * *